United States Patent [19]
Tiesler

[11] 3,990,946
[45] Nov. 9, 1976

[54] SUBSTRATE FOR THE DETERMINATION OF DESOXY-RIBONUCLEASE

[75] Inventor: Ekkehard Tiesler, Homburg, Saar, Germany

[73] Assignee: Behringwerke Aktiengesellschaft, Marburg, Lahn, Germany

[22] Filed: Sept. 3, 1974

[21] Appl. No.: 502,500

[30] Foreign Application Priority Data
Sept. 4, 1973 Germany.............................. 2344441

[52] U.S. Cl................................. 195/101; 195/99; 195/103.5 R; 424/2; 424/12
[51] Int. Cl.$^2$...................... G01N 33/00; C12K 1/04
[58] Field of Search............... 195/103.5 R, 99–102; 23/230 B; 424/2, 12

[56] References Cited
UNITED STATES PATENTS
3,042,587   7/1962   Baumgarten et al......... 195/103.5 R OTHER PUBLICATIONS
Tiesler "Diagnosis and Evaluation of Antistreptodornase B" Saarlaendisehes Aerzteblatt, Mar. 1973.

Nelson et al., J. Lab. and Clin. Med. 71, 867–873, (May, 1968).

Streitfeld et al., J. Bacteriol. 84, 77–80 (1962).

Ruth F. Itzhaki "Binding of Polylysine and Toluidine Blue to Deoxy-ribonucleoprotein" Biochem. J. 121 (1) 25p–26p, 1971.

Primary Examiner—David M. Naff
Assistant Examiner—C. A. Fan
Attorney, Agent, or Firm—Curtis, Morris & Safford

[57] ABSTRACT

A desoxy-ribonuclease substrate is prepared by boiling and homogenizing an aqueous dispersion of high molecular weight desoxy-ribonucleic acid (DNA) and 2-amino-7-dimethylamino-3-methyl diphenazthionium chloride (toluidine blue O) until a clear blue-colored solution is obtained containing a complex compound of the DNA and toluidine blue O. The substrate is used in tests for determination of desoxy-ribonuclease and it's antibodies.

3 Claims, No Drawings

SUBSTRATE FOR THE DETERMINATION OF DESOXY-RIBONUCLEASE

The present invention relates to a new substrate suitable for a simple process for determining desoxy-ribonuclease and the antibodies thereof, in particular antibodies against desoxy-ribonuclease of streptococci (antistreptodornase).

The time interval between a bacterial infection and its manifestation, the incubation period, is clincially mute, and even investigations on a laboratory scale rarely lead to an early diagnosis. An early diagnosis would be possible by direct evidence of bacterial metabolic products, and a subsequent increase in the titer of an antibody acting against these metabolic products would additionally confirm such a diagnosis. Streptococci of Group A generate a great variety of such extracellular metabolic products having an enzymatic nature, some having an immunogenic activity, for example streptolysine O, NAD-glyco-hydrolase, streptodornase, hyaluronidase and streptokinase. The determination of the antistreptolysine titer in the case of A streptococci infections is one of the classical methods; if other diseases, such as hepatitis, Lupus erythematodes, nephrosis and others, are present in the body at the same time, unspecific disturbances caused thereby may account for an increased titer of the antistreptolysine.

When A-streptococci are cultivated in an adequate nutrient medium, desoxy-ribonucleases of different electrophoretic mobility can be established in the bacteria-free supernatant of the culture. These desoxyribonucleases are designated as streptodornase A, B, C and D (DNase A, B, C and D). The major portion as to amount and activity is that of streptodornase B, so that this iso-enzyme is the most obvious to appear during a streptococci infection, owing to the formation of antibodies.

Several clinico-chemical investigations have demonstrated that the antistreptolysine titer in the case of skin infections caused by A streptococci is found to be little changed or not changed at all, while the serum level of the antistreptodornase B is found to be increased substantially.

Increasing importance in the differential diagnosis of the antistreptodornase B titer asks for easily manageable methods for the determination of the antistreptodornase level in the blood serum. Accordingly, a method has been proposed [cf. Nelson et al., J. Lab. and Clin. Med. 71, 867–873 (May, 1968)] to establish antistreptodornase by means of Methyl-Green, according to which a certain amount of desoxy-ribonuclease is incubated with the serum to be examined for antibodies. As a function of the amount of streptodornase antibodies present, the activity of desoxy-ribonuclease is reduced. When a methyl-green desoxy-ribonucleinic acid (DNA) complex is added to this mixture, this methyl-green DNA complex is split and thereby decolored as a result of the still present streptodornase activity. The readability of the reaction to be carried out by means of a dilution series of the serum is not easy and frequently leads to an erroneous determination of end points. The preparation of this reagent requires a relatively high amount of high-molecular-weight DNA.

It is known [cf. Streitfeld et al., J. Bacteriol. 84, 77–80 (1962)] that toluidine Blue O is capable of coloring an agar medium containing high-molecular-weight DNA in a blue shade, whereas areas of the agar medium, which contain DNA that has been degraded, for example, by the action of bacteria, are colored in a pink shade by toluidine Blue.

I have now found a substrate for the determination of desoxy-ribonuclease and antibodies thereof, which contains a complex compound consisting of high-molecular-weight desoxy-ribonucleinic acid (DNA) and 2-amino-7-dimethylamino-3-methyldiphenazthionium chloride (toluidine Blue O). Using a DNA complex with the meta-chromatic dyestuff 2-amino-7-dimethylamino-3-methyl-diphenazthionium chloride (toluidine Blue O) for the quantitative determination especially of streptodornase antibodies offers some advantages over the known methods. The action of DNase which is not bound to antibodies causes the dyestuff to be split off from the complex compound to from a blue-colored precipitate: The supernatant solution loses its color. Hence, when determining the anti-streptodornase titer in the sera of test persons by means of a dilution series, a simple reading permits finding that serum dilution which is just sufficient for an antibody present to bind a determined amount of DNase, and thus a blue precipitate does not yet form. It is convenient to standardize the determination of the end point by making available a serum which has a determined content of antistreptodornase B.

When determining desoxy-ribonuclease, the DNA-toluidine blue complex compound used allows the end point of the reaction to be fixed comparatively simply. To this effect, the unknown DNase activity may be measured, for example by comparing it with the activity of a determined enzyme standard which gives a blue-colored precipitate at the limit value of its activity, or a certain amount of DNase antibodies is used to establish, by means of the DNA-toluidine blue complex compound, that concentration of DNase which is no longer bound by the defined amount of anti-bodies and splits the substrate to form a blue-colored precipitate.

This invention moreover relates to the manufacture of a new substrate containing a complex compound of desoxy-ribonucleinic acid and 2-amino-7-dimethylamino-3-methyldiphenazthionium chloride and to its use in determination methods for desoxy-ribonuclease and antibodies thereof.

The process for the manufacture of the substrate is relatively simple: DNA and toluidine blue O are introduced into water or into an aqueous buffer solution, and the slight turbidity formed is dissolved by boiling and simultaneously homogenizing it. It is advantageous to prepare the substrate in a buffer solution with a pH-value approximating the reaction optimum of the DNase to be determined. Adequate pH-values range from about 4 to 9. The buffer substances to be used for this purpose are those employed for biological and physiological work, preferably those proposed by N. E. Good et al. Biochemistry 5, 467 (1966). For the neutral pH-range, trishydroxy-methylamino-methane is, for example, appropriate. For the preparation of the substrate, it is advantageous to use alkaline earth metal ions, for example in the form of water-soluble calcium or magnesium salts, in order to ensure the full activity of the enzyme acting upon the substrate, that is to say of the DNase.

If isotonicity of the substrate, for example with plasma, is to be achieved, this can be managed by adding corresponding salts, commonly sodium chloride. As DNA, a commercial preparation having a high molecular weight (more than 1,000,000) is especially useful, advantageously a DNA obtained from sperms of fish. DNA of lower molecular weight and different origin is, however, also useful. The concentration of the DNA suitably ranges from 0.01 to 0.03 %, preferably it is 0.02 %; the concentration of toluidine blue O ranges from 0.005 to 0.015 %, preferably it is 0.01 %. The concentration of the calcium or magnesium salts used preferably as substances which yield alkaline earth metal ions advantageously ranges from 0.1 to 0.5 %. These salts are to activate the DNase. The substrate prepared according to this method is a clear homogenous blue solution. The ratio of the two components in this substrate may vary greatly within reasonable limits; advantageously it is about 2 parts by weight of DNA to 1 part by weight of toluidine blue O, a 10 % deviation from this ratio being of no consequence.

In many cases, it may be convenient in carrying out the test to dilute the solution with a dilution liquid containing a buffer system, which is to be selected in accordance with the pH optimum of the DNase to be determined. In addition to the buffer substances proposed by Good et al. (1966) and other buffer systems useful for biochemical work, imidazole-hydrochloric acid has proved to be suitable for the determination of DNases at a pH of from 6.0 to 8.0. The dilution liquid advantageously contains one of the stabilizers frequently used for operations in dilute enzyme solutions. Proteins, for example albumins, gelatins and derivatives thereof, are also useful for this purpose as are polyhydroxy compounds, for example dextrans and sugar.

The substrate of the invention is especially suitable in micro methods for the determination of streptodornase antibodies in clinical diagnosis, in particular for the micro titer plates used in serology.

There is, however, no reason why the substrate should not be used in a macro test using increased volumes in the test tubes. The substrate may also be used as disclosed above to determine the DNase.

In a comparative test for the antistreptodornase B titers in healthy people and patients who have gone through an infection caused by streptococci, the test system cited in the Examples is used to find a marked increase of antistreptodornase B in the patients.

Being normally below a ratio of 1 : 200 in healthy persons, serum titers of the streptodornase antibodies exceeding this ratio may, inter alia, allow the diagnosis of rheumatic fever, infection of the upper air passages or Glomerulonephritis.

The following Examples illustrate the invention.

EXAMPLE 1

Preparation of the DNA substrate 0.3 Gram of trishydroxymethylamino-methane, 0.5 g of NaCl, 15 mg of purified DNA and 0.05 ml of a 0.01M calcium chloride solution were added to 100 ml of distilled water. The pH-value of the solution was adjusted to 7.0 by means of 1.0 ml of 0.1N HCl. The mixture was boiled for about 10 seconds, whereupon a homogeneous clear solution was obtained. 0.3 ml of a 0.1M toluidine blue O solution which distributed homogenously in the first solution was then added to the hot solution.

After cooling, the DNA substrate was ready for activity determinations. Should flakes appear on storage for a prolonged time, the substrate solution is to be boiled up again for a short time prior to use.

EXAMPLE 2

Preparation of the streptodornase B antigen

DNase which had been obtained from a 16-hour culture of an A streptococci strain forming DNase B and purified according to known methods was standardized to 30 units per ml (measured in a Brookfield microrotation viscosimeter) (Calculated on DNase I from pancreas). Immediately prior to the test, the antigen solution was diluted at a ratio of 1 : 30.

EXAMPLE 3

Preparation of the dilution liquid 400 ml of an aqueous solution of bovine albumin containing 250 mg of bovine albumin per 100 ml were mixed with 100 ml of a 0.25 M imidazole-HCl buffer of pH 8.0, containing 1.47 g of calcium chloride dihydrate and 0.6 g of magnesium sulfate per liter.

EXAMPLE 4

Determination of the streptodornase B antibodies in sera

Determination was made as follows:

In micro titer plates, 25 $\mu$l of the dilution liquid as prepared in Example 3 were filled into Cup 2 of the first series, two times 25 $\mu$l of the same dilution liquid were filled into Cup 3, and 25 $\mu$l each of the dilution liquid were filled into the following cups. Subsequently, 25 $\mu$l each of a 1 : 50 dilution of a serum taken from healthy persons were filled into cups 1, 2 and 3. Starting from cup 2, 25 $\mu$l each of the serum dilution obtained were conveyed by pipet to cup 4 and further to cup 6 and so on to cups 8, 10 and 12. Starting from cup 3, 25 $\mu$l each of the corresponding serum dilution were conveyed over to cup 5 and also further to cups 7, 9 and 11. Subsequently, 25 $\mu$l each of the serum dilution were eliminated from cups 3, 11 and 12. Thus, starting from cup 1, a dilution series of 1 : 50, 100, 150, 200, 300, 400, 600, 800, 1200, 1600, 2500 and 3200 was obtained. The same dilution series were made for the sera of patients to be determined in series 2 and 3 of the micro titer plate. Then, 25 $\mu$l of the standard antigen dilution as obtained in Example 2 were added to each of the 25 $\mu$l serum dilution and allowed to stand for 4 minutes on a shaking device. Finally, 50 $\mu$l of the substrate solution as prepared in Example 1 were added to each of the dilutions.

The mixture was then incubated at 37° C. The formation of a blue-colored precipitate indicated the dilution of the antibodies present in the serum, which was no longer able to bind the DNase added. As soon as a control serum accompanying the test mixture and having a fixed titer of 1 : 150 caused the precipitate to form up to the dilution of 1 : 150, the values were read off. In this exemplified specimen, a precipitate formed throughout the first series. Hence, the titer was less than 1 : 50. In the second series, a precipitate formed in cup 4; hence, the titer was 1 : 150. In the third series, a precipitate formed starting from cup 8, corresponding to a titer of 1 : 600.

EXAMPLE 5

Determination of desoxy-ribonuclease

In the first series of a micro titer plate, 50 microliters of a culture solution of streptococci, which had been filtered under sterile conditions, were filled into cup 1.

The following cups were filled with 25 microliters of the dilution liquid as prepared according to Example 3. By conveying 25 microliters each from the first to the second cup, further from the second to the third cup and so on, a dilution series of the following ratio was obtained: 1 : 2, 1 : 4, 1 : 8, and so on.

A DNase of known activity was diluted in the second series of the micro titer plate in the same manner. To 25 microliters each of the enzyme dilutions, 50 microliters of the substrate solution as prepared in Example 1 were added, whereupon the mixture was incubated at 40° C for 3 hours. The formation of a blue-colored precipitate was taken as an indicator for the enzyme activity. The streptococci culture filtrate formed a precipitate up to cup 8, corresponding to a dilution of 1 : 128.

The accompanying standard DNase in this test system always caused precipitation up to cup 10, corresponding to a dilution of 1 : 512.

The result of this test shows that the culture filtrate to be tested has a DNase activity of 25 % of the standard.

I claim:
1. The method of making a solubilized complex compound of high-molecular-weight desoxy-ribonucleic acid (DNA) and 2-amino-7-dimethyl-amino-3-methyl-diphenazthionium chloride (toluidine blue O), which comprises boiling and homogenizing an aqueous dispersion of high-molecular weight DNA and toluidine blue O in a weight ratio of about 2:1, until a clear homogenous blue-colored solution is obtained.
2. The method as in claim 1 wherein alkali metal ions are added to the dispersion in a concentration from 0.1 to 0.5 percent.
3. The method as in claim 1 wherein the concentration of DNA is from 0.01 to 0.03 percent and that of toluidine blue O is from 0.005 to 0.015 percent in said solution.

* * * * *